US00PP26173P3

(12) United States Plant Patent
Mazzardis

(10) Patent No.: US PP26,173 P3
(45) Date of Patent: Dec. 1, 2015

(54) BLUEBERRY PLANT, EB 8-46

(50) Latin Name: ***Vaccinium* Hybrid**
Varietal Denomination: EB 8-46

(71) Applicant: Vincent Mazzardis, Joondalup (AU)

(72) Inventor: Vincent Mazzardis, Joondalup (AU)

(73) Assignee: Prunus Persica Pty Ltd & Rolfe Nominees Pty Ltd (AU)

( * ) Notice: Subject to any disclaimer, the term of this patent is extended or adjusted under 35 U.S.C. 154(b) by 86 days.

(21) Appl. No.: 13/998,668

(22) Filed: Nov. 21, 2013

(65) Prior Publication Data

US 2014/0150142 P1 May 29, 2014

(30) Foreign Application Priority Data

Nov. 29, 2012 (AU) ..... 2012/260

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU 2012/260 11/2012

OTHER PUBLICATIONS

PLUTO Plant Variety DAtabase Apr. 15, 2015. p. 1.*
Plant Varieties Journal, vol. 26, Issue 4.

* cited by examiner

*Primary Examiner* — Annette Para
(74) *Attorney, Agent, or Firm* — Randall Danskin PS

(57) ABSTRACT

A new and distinct variety of blueberry plant, which is denominated varietally as 'EB 8-46' is described, and which produces extra large sized fruit, and which further has a dry small picking scar, very good fruit flavor and an earlier flowering and fruit production dates when grown under the ecological conditions prevailing in Yanchep Springs, Western Australia.

3 Drawing Sheets

Latin name: '*Vaccinium* Hybrid'.
Varietal denomination: 'EB 8-46'.

RELATED APPLICATION DATE

The present application claims priority to Australia Plant Breeders Rights Application, Serial No. 2012/260 and which was filed on Nov. 29, 2012.

BACKGROUND OF THE NEW VARIETY

The present invention relates to a new, novel, and distinct variety of blueberry plant '*Vaccinium* Hybrid,' and which has been denominated varietally as 'EB 8-46', hereinafter.

ORIGIN AND ASEXUAL REPRODUCTION OF THE NEW VARIETY

The present variety of blueberry plant resulted from an ongoing development program of plant breeding. The purpose of this program is to improve the commercial quality of various plant varieties by creating and releasing promising selections of plants including blueberries. To this end, I have made both controlled and hybrid cross-pollinations each year in order to produce resulting plant populations from which improved progenies are evaluated and selected.

The blueberry plant 'EB 8-46' was derived from a controlled cross-pollination employing the blueberry plant 'BB-5' [unpatented], and the pollen parent was 'SB-1' [also unpatented] during the 2005 growing season and which took place at Yanchep Springs, Yanchep, Western Australia. The seed parent 'BB-5' is characterized by an semi-spreading growth habit, an early season of flowering, and which further produces medium-sized fruit. The pollen parent 'SB-1' on the other hand, is characterized by a spreading growth habit, an early season of flowering, and which produces relatively large sized fruit. Seed from the seed parent, and which was derived following the aforementioned cross-pollination, produced about 500 plants. These plants were then grown, and the first fruit was evaluated during the 2007 growing season. Further, an additional assessment of these same plants took place in 2008. The new variety, 'EB 8-46' was then selected at that time for further asexual reproduction and evaluation. The present variety was asexually reproduced by cuttings, and the plants produced from this first asexual propagation were evaluated during the 2009 through 2013 growing seasons. The asexually reproduced plants were true to the original plant, and it was concluded at that time that 'EB 8-46' was a new, novel and distinct variety of blueberry plant.

In relative comparison to the closest known variety, that being the 'Sharpeblue' blueberry plant [unpatented], the present variety produces early maturing, very large fruit. The new variety of blueberry plant further has an intermediate growth habit, and additionally produces oblate shaped fruit. In contrast, the 'Sharpeblue' blueberry plant produces fruit which are mature for harvesting and shipment from a date which is considered early to approximately middle of the growing season. Moreover, the 'Sharpeblue' blueberry plant produces fruit which have an average to medium size, and also has an intermediate growth habit. It should be noted that the new variety is distinguishable from its parents, and that of the 'Sharpeblue' blueberry plant by producing extra large sized fruit, having a dry, small, picking scar, very good fruit flavor and early flowering and fruit production dates.

BRIEF DESCRIPTION OF THE DRAWING

The accompanying drawings, which are provided are color photographs of the new blueberry plant.

Figure 1:
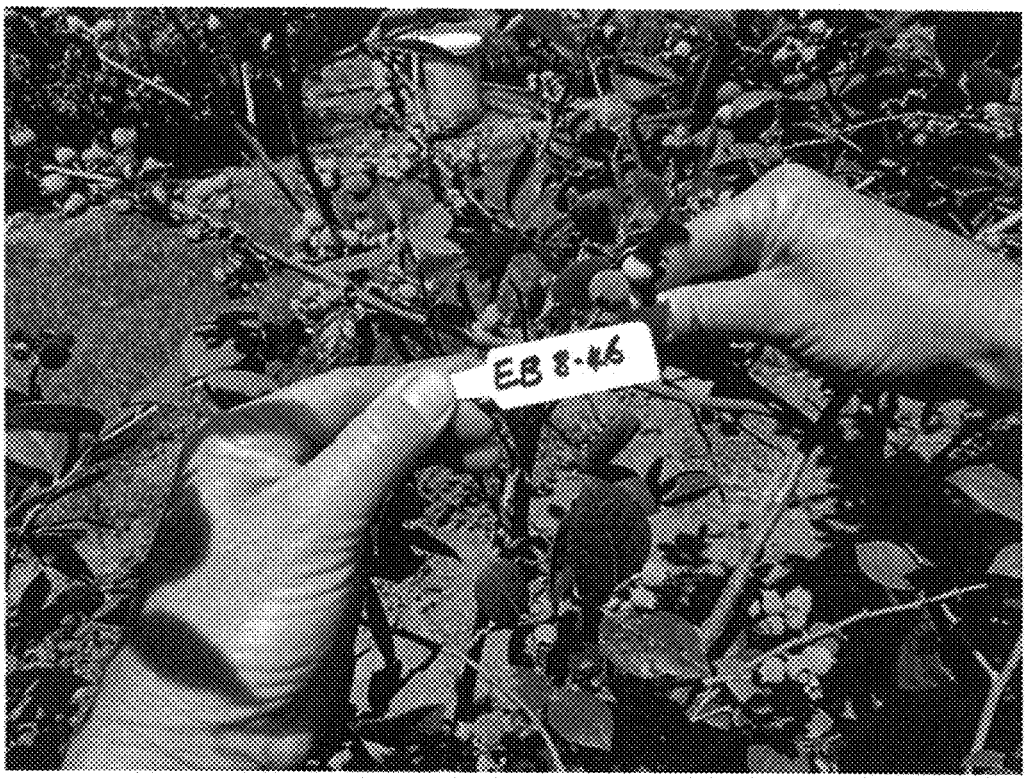
FIG. 1 depicts several mature fruit of the new variety and which is sufficiently matured for harvesting and shipment. Further, FIG. 1 additionally depicts a typical shoot bearing leaves and several separate leaves showing the dorsal and ventral coloration thereof, as well as the growth habit of the new plant.
Figure 2:
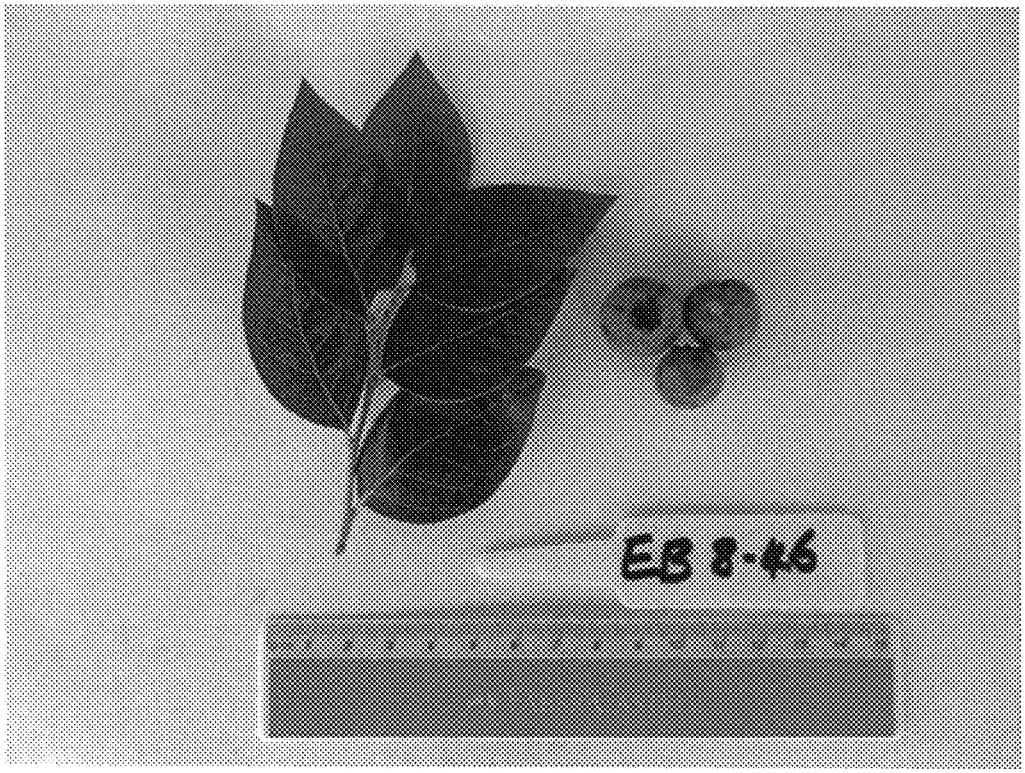
FIG. 2 depicts a twig bearing typical leaves, and several fruit of the new variety.
Figure 3:
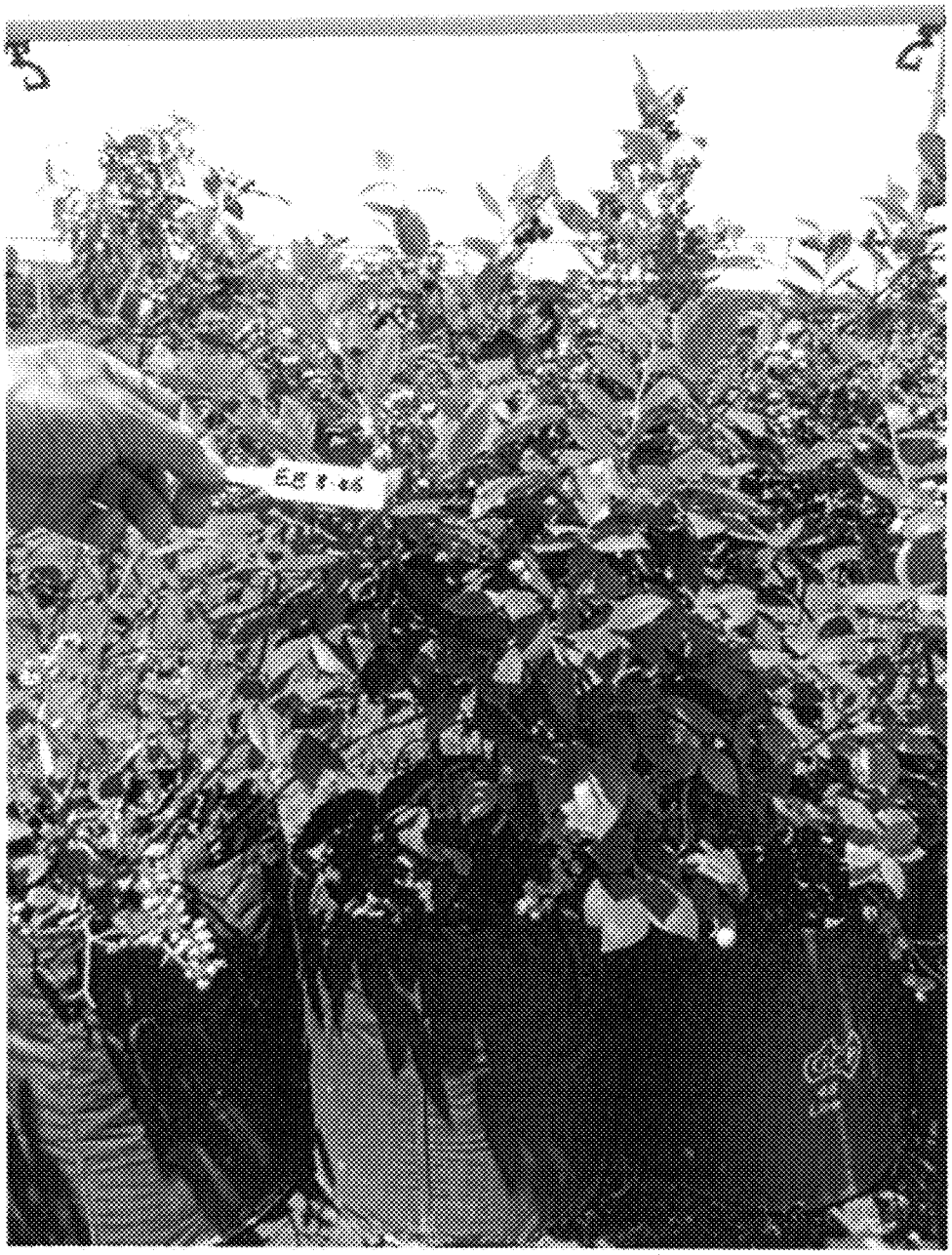
FIG. 3 depicts the growth habit of the new plant.

The colors in these photographs are as nearly true as is reasonably possible in a color representation of this type. Due to chemical development, processing and printing, the leaves and fruit depicted in these photographs may or may not be accurate when compared to the actual specimen. For this reason, future color references should be made to the descriptions as provided hereinafter.

NOT A COMMERCIAL WARRANTY

The following detailed description has been prepared to solely comply with the provisions of 35 U.S.C. §112, and does not constitute a commercial warranty (either expressed or implied) that the present variety will, in the future, display the botanical, horticultural, or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

DETAILED DESCRIPTION

Referring more specifically to the botanical details of this new and distinct variety of blueberry plant, the following has been observed during the sixth fruiting season under the ecological conditions prevailing at the farm of the inventor, and which is located near Yanchep Springs, Western Australia.

PLANT

Plant vigor: The present variety of blueberry is considered to be average to strong with regard to plant vigor. This is similar to the closest known variety, that being the 'Sharpeblue' blueberry plant [unpatented].

Plant growth habit: Considered intermediate to strong in relative comparison other known varieties. This is similar to the growth habit as exhibited by the 'Sharpeblue' blueberry plant when grown under similar conditions.

Color:

*One year old shoots.*—Yellow-Green (RHS146D). This color is not distinctive of the new variety and is similar to the color as expressed by the 'Sharpeblue' blueberry plants when grown under similar conditions.

Average plant size: About 1.5 meters in height; and about 1.2 meters in width.

Internode length:

*One year old shoots.*—Considered medium for the species. This is in contrast to the same characteristic as expressed by the 'Sharpeblue' blueberry plant which exhibits a medium to medium-long internode length.

LEAF

Leaf length:

*Generally.*—Considered medium for the species, about 62 mm. This characteristic is in contrast to the growth characteristic as expressed by the 'Sharpeblue' blueberry plant which expresses a medium to long length.

Average leaf width: About 39 mm.

Leaf ratio:

*Length/width.*—Considered medium for the species. This is in contrast to the growth characteristic as expressed by the Sharpeblue blueberry plant which is considered medium to broad.

Leaf shape:

*Generally.*—Considered ovate. This trait is similar to the growth characteristic as expressed by the 'Sharpeblue' blueberry plant when grown under similar conditions.

Leaf color:

*Dorsal surface.*—Green (RHS 137B). This color is not distinctive of the variety and is similar to the color as expressed by the 'Sharpeblue' blueberry plant when grown under similar conditions.

Leaf color:

*Ventral surface.*—Green (RHS 137D).

Color intensity:

*Dorsal surface.*—The green color intensity as expressed in the leaves of the present variety appear noticeably darker (medium to dark) in relative comparison to the green color of the leaves as expressed by the growth habit of the 'Sharpeblue' blueberry plant. This is a distinguishing characteristic of the present variety.

Leaf margin:

*Generally.*—The leaf margin of the present variety is considered entire. This same growth characteristic is expressed by the 'Sharpeblue' blueberry plant.

FLOWER

Flowers:

*Generally.*—Time of vegetative bud burst considered early for the species, this is similar to the trait as expressed by the 'Sharpeblue' blueberry plant.

Time of flowering:

*One year old shoots.*—Considered early. This is similar to the trait as expressed by the 'Sharpeblue' blueberry plant.

Timing of flowering on current year's shoots: Considered early for the species.

Flower color: White (RHS N155D).

Time of beginning of ripening on one year old shoots: Considered early for the species. This is in contrast to the trait as expressed by the closest known variety where the ripening is considered early to medium for the species.

Time of beginning of ripening on current year shoots: Considered early. This is in contrast to the early to medium date as expressed by the 'Sharpeblue' blueberry plant.

Flower bud:

*Anthocyanin coloration.*—Considered very weak for the species. A similar characteristic is expressed by the 'Sharpeblue' blueberry plant when grown under similar ecological conditions.

Inflorescence length: Considered medium for the species. The average flower length is about 12 mm. This characteristic is not distinctive of the variety.

Average flower width: About 7 mm.

Corolla shape: Considered urceolate. This is similar to the characteristic as expressed by the 'Sharpeblue' blueberry plant.

Flower size:

*Corolla tubes.*—Considered medium for the species. This is in contrast to the growth characteristic as expressed by the 'Sharpeblue' blueberry plant when grown under similar conditions and where the Corolla tubes are medium to large.

Corolla tube coloration:

*Anthocyanin.*—Considered weak to very weak. This is in contrast to the growth characteristic as expressed by the 'Sharpeblue' blueberry plant which appears merely weak.

Corolla tube:

*Ridges.*—Present. This growth characteristic is also expressed by the 'Sharpeblue' blueberry plant when grown under similar conditions.

FRUIT

Fruit cluster density: Considered medium to dense for the species. This fruit cluster density is dissimilar to the growth characteristic as expressed by the 'Sharpeblue' blueberry plant when grown under similar conditions and where the fruit cluster density is considered dense to very dense.

Unripe fruit:

*Color.*—The green coloration as expressed by the unripe fruit of the present variety is considered medium in intensity, (RHS 144D). This is in contrast to the fruit color as seen on unripe fruit of the 'Sharpeblue' blueberry plant when grown under similar conditions. In that case, the unripe fruit have a light to medium green color.

Fruit size:

*Generally.*—The present variety produces very large fruit in contrast to the medium sized fruit as produced by the closest known variety, that being the 'Sharpeblue' blueberry plant. In this regard the fruit has an average diameter of about 21 mm.

Fruit shape:

*Longitudinal sectional view.*—Considered oblate. This is similar to the shape of the fruit which are produced by the 'Sharpeblue' blueberry plant.

Fruit flesh color: Yellow-Green (RHS 145B).

Sepal position/altitude: Considered semi-erect in contrast to the orientation and attitude of the sepals when seen on the 'Sharpeblue' blueberry plant when grown under similar conditions.

Sepal type: The present variety has an incurring shaped sepal as compared to the straight type of sepal as expressed in the growth habit of the 'Sharpeblue' blueberry plants when grown under similar ecological conditions.

Fruit diameter:

*Calyx basin.*—Medium for the species. This is in contrast to the growth habit as expressed by the 'Sharpeblue' blueberry plant when grown under similar conditions, and where the diameter of the Calyx basin is considered small to medium.

Calyx basin/depth: Considered shallow to medium in depth, about 8 mm in diameter, and about 3.5 mm in depth. This is in contrast to the growth habit as expressed by the 'Sharpeblue' blueberry plant and when grown under similar conditions and where this depth is considered merely medium.

Average corolla length.—About 9.5 mm.

Intensity of fruit bloom: Considered very strong for the variety. This is in contrast to the strong bloom intensity of the 'Sharpeblue' blueberry plant when grown under similar ecological conditions.

Fruit skin color: Considered very dark blue and similar to the coloration as seen on the fruit of the 'Sharpeblue' blueberry plant when grown under similar conditions, (RHS 203D).

Fruit firmness:

*Generally.*—The present variety produces very firm fruit in contrast to the medium firmness fruit as produced by the 'Sharpeblue' blueberry plant when grown under similar conditions.

Seed color: Grey-Brown: (RHS N199B).

Fruit sweetness:

*Generally.*—The present variety produces fruit having a high degree of sweetness in contrast to the average sweetness as expressed by the fruit produced by the Sharpeblue Blueberry Plant when grown under similar conditions.

Fruit acidity:

*Generally.*—Considered low for the species. The low acidity, as expressed by the fruit grown by the present variety, is in contrast to the somewhat average or medium acidity as expressed by the fruit of the 'Sharpeblue' blueberry plant when grown under similar conditions.

Plant:

*Fruiting type.*—Fruit appears on one year old and current season shoots. This is similar to the growth habit as expressed by the 'Sharpeblue' blueberry plant when grown under similar conditions.

Date of ripening of fruit on current year's shoots: Considered early for the species and earlier in time relative to the same growth habit as expressed by the 'Sharpeblue' blueberry plant when grown under similar conditions. The beginning of fruit ripening on one year old shoots is considered early for the species and in contrast to the later date as expressed by the growth habit of the 'Sharpeblue' blueberry plant.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep Springs, Western Australia, it should be understood that the variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A new and distinct variety of blueberry plant, substantially as illustrated and described and which is characterized principally as to novelty by producing extra large size fruit, which has a small, dry picking scar and very good fruit flavor, and an earlier flowering and fruit production dates when grown under the ecological conditions prevailing in and near Yanchep Springs, Western Australia.

* * * * *